(12) United States Patent
Ferek-Petric

(10) Patent No.: US 6,873,870 B2
(45) Date of Patent: Mar. 29, 2005

(54) METHODS FOR ADJUSTING CARDIAC DETECTION CRITERIA AND IMPLANTABLE MEDICAL DEVICES USING SAME

(75) Inventor: Bozidar Ferek-Petric, Zagreb (HR)

(73) Assignee: Medtronic, Inc., Minneapolis, MN (US)

(*) Notice: Subject to any disclaimer, the term of this patent is extended or adjusted under 35 U.S.C. 154(b) by 49 days.

(21) Appl. No.: 09/843,914

(22) Filed: Apr. 30, 2001

(65) Prior Publication Data

US 2002/0188215 A1 Dec. 12, 2002

(51) Int. Cl.⁷ .......................................... A61B 5/0468

(52) U.S. Cl. ...................................................... 600/518

(58) Field of Search .................. 600/509, 515, 600/516, 518, 519, 521; 607/4–7, 9, 11, 14, 17, 18, 23–25

(56) References Cited

U.S. PATENT DOCUMENTS

| | | |
|---|---|---|
| 4,316,472 A | 2/1982 | Mirowski et al. |
| 4,375,817 A | 3/1983 | Engle et al. |
| 4,379,459 A | 4/1983 | Stein |
| 4,384,585 A | 5/1983 | Zipes |
| 4,476,868 A | 10/1984 | Thompson |
| 4,556,063 A | 12/1985 | Thompson et al. |
| 4,577,633 A | 3/1986 | Berkovits et al. |
| 4,587,970 A | 5/1986 | Holley et al. |
| 4,726,380 A | 2/1988 | Vollmann et al. |
| 4,727,877 A | 3/1988 | Kallock |
| 4,800,883 A | 1/1989 | Winstrom |
| 4,821,723 A | 4/1989 | Baker, Jr. et al. |
| 4,830,006 A | 5/1989 | Haluska et al. |
| 4,880,005 A | 11/1989 | Pless et al. |
| 4,949,719 A | 8/1990 | Pless et al. |
| 4,953,551 A | 9/1990 | Mehra et al. |
| 5,099,838 A | 3/1992 | Bardy |
| 5,117,824 A | 6/1992 | Keimel et al. |
| 5,129,394 A | 7/1992 | Mehra |
| 5,131,388 A | 7/1992 | Pless |
| 5,144,949 A | 9/1992 | Olson |
| 5,158,078 A | 10/1992 | Bennett et al. |
| 5,163,427 A | 11/1992 | Keimel |
| 5,188,105 A | 2/1993 | Keimel |
| 5,199,428 A | 4/1993 | Obel et al. |
| 5,207,218 A | 5/1993 | Carpentier et al. |
| 5,257,621 A * | 11/1993 | Bardy et al. ................... 607/5 |
| 5,269,298 A | 12/1993 | Adams et al. |
| 5,271,408 A | 12/1993 | Breyer et al. |
| 5,312,441 A | 5/1994 | Mader et al. |
| 5,312,453 A | 5/1994 | Shelton et al. |
| 5,314,430 A | 5/1994 | Bardy |
| 5,330,507 A | 7/1994 | Schwartz |

(List continued on next page.)

FOREIGN PATENT DOCUMENTS

WO    WO 92/18198    10/1992

OTHER PUBLICATIONS

Arzbaecher et al., "Automatic Tachycardia Recognition," *PACE*, 541–547 (May–Jun. 1984).
Olson et al., "Onset and Stability for Ventricular Tachyarrhythmia Detection in an Implantable Pacer–Cardioverter–Defibrillator," *Computers in Cardiology*, IEEE Computer Society Press, 167–170 (Oct. 7–10, 1986).

*Primary Examiner*—Angela D. Sykes
*Assistant Examiner*—Frances P. Oropeza
(74) *Attorney, Agent, or Firm*—Paul H. McDowall; Girma Wolde-Michael

(57) ABSTRACT

Implantable medical devices and methods of tachycardia detection that provide adjustable detection criteria based upon a hemodynamic parameter. In some embodiments, the apparatus and methods provide for detection and delivery of therapy for hemodynamically stable and hemodynamically unstable tachycardias by varying a number of intervals detected (NID) threshold based on hemodynamic measurements.

15 Claims, 9 Drawing Sheets

U.S. PATENT DOCUMENTS

| | | |
|---|---|---|
| 5,331,966 A | 7/1994 | Bennett et al. |
| 5,342,404 A * | 8/1994 | Alt et al. ................ 607/6 |
| 5,354,316 A | 10/1994 | Keimel |
| 5,354,319 A | 10/1994 | Wyborny et al. |
| 5,370,667 A | 12/1994 | Alt |
| 5,403,355 A | 4/1995 | Alt |
| 5,431,685 A | 7/1995 | Alt |
| 5,458,622 A * | 10/1995 | Alt ................ 607/15 |
| 5,545,186 A | 8/1996 | Olson et al. |
| 5,690,686 A | 11/1997 | Min et al. |
| 5,785,657 A | 7/1998 | Breyer et al. |
| 5,799,350 A | 9/1998 | Ferek-Petric et al. |
| 5,800,465 A | 9/1998 | Thompson et al. |
| 6,171,252 B1 | 1/2001 | Roberts |

\* cited by examiner

METHODS FOR ADJUSTING CARDIAC DETECTION CRITERIA AND IMPLANTABLE MEDICAL DEVICES USING SAME

FIELD OF THE INVENTION

The present invention relates to implantable medical devices and methods for cardiac stimulation. More particularly, the present invention pertains to implantable medical devices and methods that employ adjustable detection criteria.

BACKGROUND

Implantable medical devices, such as pacing apparatus, generally include detection algorithms to detect various types of heart conditions, e.g., ventricular fibrillation (VF), ventricular tachycardia (VT), supra-ventricular tachyarrhythmia (SVT), etc., that require employment of therapy. For example, detection algorithms may be based on heart rate, or in other words R—R intervals, alone or in combination with other additional criteria, such as sudden onset criteria, rate stability criteria, and QRS width. For example, dual chamber pacemaker-cardioverter-defibrillators (PCDs) may be able to differentiate supra-ventricular tachyarrhythmias from ventricular tachycardias using an algorithm that processes atrial and/or ventricular EGM signals. In many cases, to increase detection accuracy and/or to distinguish various types of arrhythmias, such as various types of ventricular tachyarrhythmias, devices may include a type of hemodynamic sensor, e.g., an intra-cardial blood pressure sensor and/or a flow sensor.

A common approach to programming PCDs uses the specification of discrete heart rate zones (e.g., R—R interval zones) for ventricular fibrillation (VF) and various types of ventricular tachycardia (VT). Each rate zone for the detection algorithms, for example, may be defined using different heart rates and, correspondingly, different R—R interval values. For example, a PCD may have three different heart rate zones: VT, fast VT, and VF. Each of these rate zones, e.g., VT, fast VT, and VF, may be treated by a separately defined therapy.

Moreover, therapy for any particular type of arrhythmia may be delayed until a preprogrammed number of consecutive counts or intervals are obtained in which the heart rate detected is within a particular rate zone. The number of intervals detected (NID) (e.g., the number of R—R intervals detected in a particular rate zone) must reach a set value before therapy will be delivered. This threshold may differ for each identified arrhythmia, e.g., may be programmable in wide ranges separately for VF, fast VT, and VT.

Generally, systems that depend upon the aforementioned heart rate criteria are capable of discriminating tachycardia in a greater or lesser degree from normal heart rate. However, such systems may have difficulty discriminating hemodynamically stable tachycardia from hemodynamically unstable tachycardia.

Hemodynamically unstable tachycardia is generally accompanied by a decrease in the mean blood pressure. Hemodynamically unstable tachycardia may provoke syncope due to such a systemic blood pressure drop, which may be sudden or develop successively. Hemodynamically stable tachycardia, on the other hand, generally is not accompanied by a systemic blood pressure drop, and therefore, usually causes some kind of palpitations but not syncope. In clinical practice, hemodynamically stable tachycardia may be successfully treated by anti-tachycardia pacing, e.g., extra stimuli or bursts of stimuli. Such hemodynamically stable tachycardia is usually slow, but if not terminated, it may accelerate and become hemodynamically unstable.

For pacing devices, such as PCDs, with programmed heart rate zones for detection of various types of tachyarrhythmias, determining the type of and the time for delivery of therapy for hemodynamically stable and/or unstable tachycardia may be problematic. For example, a higher NID threshold may be desirable to increase the specificity for detection of sustained tachycardia. However, this also increases the time between tachyarrhythmia onset and the delivery of therapy. Therefore, although desirable for detection of hemodynamically stable tachyarrhythmias, such a higher NID threshold may not be able to detect hemodynamically unstable tachycardia as quickly as would be desired. Further, a lower NID threshold may be convenient for detection of hemodynamically unstable tachycardia, but undesirable for detection of hemodynamically stable tachyarrhythmias, leading to therapy that may inadvertently be delivered too early when the tachycardia is hemodynamically stable and unsustained.

Table I below lists U.S. Patents relating to detection of various types of tachyarrhythmias.

TABLE I

| U.S. Pat. No. | Inventor | Issue Date |
| --- | --- | --- |
| 5,129,394 | Mehra | Jul. 14, 1992 |
| 5,257,621 | Bardy et al. | Nov. 2, 1993 |
| 5,342,404 | Alt et al. | Aug. 30, 1994 |
| 5,370,667 | Alt | Dec. 6, 1994 |
| 5,403,355 | Alt | Apr. 4, 1995 |
| 5,431,685 | Alt | Jul. 11, 1995 |
| 5,458,622 | Alt | Oct. 17, 1995 |

All references listed in Table I, and elsewhere herein, are incorporated by reference in their respective entireties. As those of ordinary skill in the art will readily appreciate upon reading the Summary of the Invention, Detailed Description of the Embodiments, and claims set forth below, at least some of the devices and methods disclosed in the references of Table I and elsewhere herein may be modified advantageously by using the teachings of the present invention. However, the listing of any such references in Table I, or elsewhere herein, is by no means an indication that such references are prior art to the present invention.

SUMMARY OF THE INVENTION

The present invention has certain objects. That is, various embodiments of the present invention provide solutions to one or more problems existing in the art with respect to PCD detection and therapeutic delivery techniques and, in particular, detecting hemodynamically stable or unstable tachycardia and delivery of appropriate treatment. One such problem involves discriminating between hemodynamically stable tachycardia and hemodynamically unstable tachycardia. Other problems include the need to deliver the appropriate therapy in a timely manner without compromising detection accuracy. Further, for example, other problems include inhibiting inappropriate therapies that may cause hemodynamic instability and unneeded discomfort.

In comparison to known detection techniques for PCDs, various embodiments of the present invention may provide certain advantages. For instance, more accurate discrimination between hemodynamically stable and hemodynamically unstable tachycardia is achieved. Further, the present invention allows for rapid detection of hemodynamically unstable tachycardia without compromising accurate detection of, and delivery of appropriate therapy for, hemodynamically stable tachycardia.

Some embodiments of the present invention may provide one or more of the following features for detecting a tachycardia: sensing a heart rate; comparing the heart rate to a heart rate threshold value; initiating an adjustable number of intervals detected (NID) threshold upon detecting the heart rate greater than the heart rate threshold value; resetting the adjustable NID threshold based on at least a first measurement of a hemodynamic parameter; counting a consecutive number of intervals in which the heart rate is greater than the heart rate threshold value; detecting tachycardia if the consecutive number of intervals satisfies the adjustable NID threshold; delivering a first therapy; comparing a second heart rate to the heart rate threshold value after delivery of the first therapy; resetting the adjustable NID threshold to a second adjustable NID threshold based on at least a second measurement of the hemodynamic parameter; counting a consecutive number of intervals in which the second heart rate is greater than the heart rate threshold value; and delivering a second therapy if the consecutive number of intervals in which the second heart rate is greater than the heart rate threshold value satisfies the second adjustable NID threshold. Embodiments of the present invention may further include one or more of the following features: storing one or more parameters relating to the tachycardia; resetting the adjustable NID threshold based on a blood pressure; reducing the adjustable NID threshold in response to a drop in blood pressure; resetting the adjustable NID threshold based on a blood flow; and resetting the adjustable NID threshold based on a physiologically-sensed condition. Other features may include sensing at least one first R—R interval; comparing the at least one first R—R interval to an interval threshold value; initiating a first adjustable number of intervals detected (NID) threshold upon detecting the at least one first R—R interval less than the interval threshold value; sensing a first hemodynamic measurement; counting a first consecutive number of R—R intervals in which each of the first consecutive number of R—R intervals is less than the interval threshold value; and detecting tachycardia if the first consecutive number of R—R intervals is equal to or greater than the first adjustable NID threshold.

Further, some embodiments of the present invention include one or more of the following features for a pacing apparatus: sensing and pacing circuitry for sensing cardiac activity and generating pacing pulses; a hemodynamic sensor; controller circuitry in communication with the hemodynamic sensor; controller circuitry that is operable to sense a heart rate using the sensing and pacing circuitry, compare the heart rate to a heart rate threshold value, initiate an adjustable number of intervals detected (NID) threshold upon detecting a heart rate greater than the heart rate threshold value, reset the adjustable NID threshold based on at least a first measurement of a hemodynamic parameter, count a consecutive number of intervals in which the heart rate is greater than the heart rate threshold value, and detect tachycardia if the consecutive number of intervals satisfies the adjustable NID threshold; controller circuitry that is operable to sense at least one first R—R interval, compare the at least one first R—R interval to an interval threshold value, initiate a first adjustable number of intervals detected (NID) threshold upon detecting the at least one first R—R interval less than the interval threshold value, sense a first hemodynamic measurement, reset the first adjustable NID threshold based on the first hemodynamic measurement, count a first consecutive number of R—R intervals in which each of the first consecutive number of R—R intervals is less than the interval threshold value, detect tachycardia than the first consecutive number of R—R intervals is equal to or greater than the first adjustable NID threshold, and deliver a first therapy; and controller circuitry that is operable to sense at least one second R—R interval, compare the at least one second R—R interval to the interval threshold value, initiate a second adjustable number of intervals detected (NID) threshold upon detecting the at least one second R—R interval less than the interval threshold value, sense a second hemodynamic measurement, reset the second adjustable NID threshold based on the second hemodynamic measurement, count a second consecutive number of intervals in which each of the second consecutive number of R—R intervals is less than the interval threshold value, detect tachycardia if the second consecutive number of intervals is equal to or greater than the second adjustable NID threshold, and deliver a second therapy.

The above summary of the invention is not intended to describe each embodiment or every implementation of the present invention. Rather, a more complete understanding of the invention will become apparent and appreciated by reference to the following detailed description and claims in view of the accompanying drawings.

BRIEF DESCRIPTION OF THE DRAWINGS

The present invention will be further described with reference to the drawings, wherein.

DETAILED DESCRIPTION OF THE EMBODIMENTS

Figure 1:
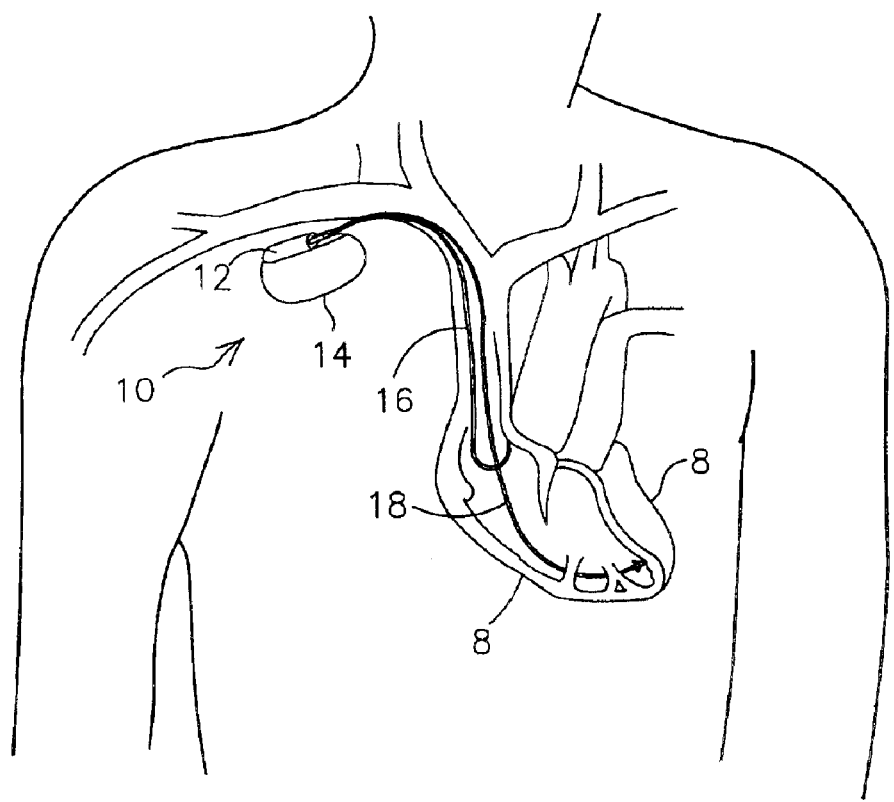
FIG. 1 is an implantable medical device (IMD) in accordance with one embodiment of the invention, wherein the IMD is shown implanted within the body of a patient.

FIG. 1 is a simplified schematic view of one embodiment of implantable medical device ("IMD") 10 of the present invention. IMD 10 shown in FIG. 1 is a pacemaker comprising at least one of pacing and sensing leads 16 and 18 attached to hermetically sealed enclosure 14 and implanted near human or mammalian heart 8. Pacing and sensing leads 16 and 18, sense electrical signals attendant to the depolarization and repolarization of the heart 8, and further provide pacing pulses for causing depolarization of cardiac tissue in the vicinity of the distal ends thereof. Leads 16 and 18 may have, for example, unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al. and U.S. Pat. No. 5,144,949 to Olson.

Figure 2:
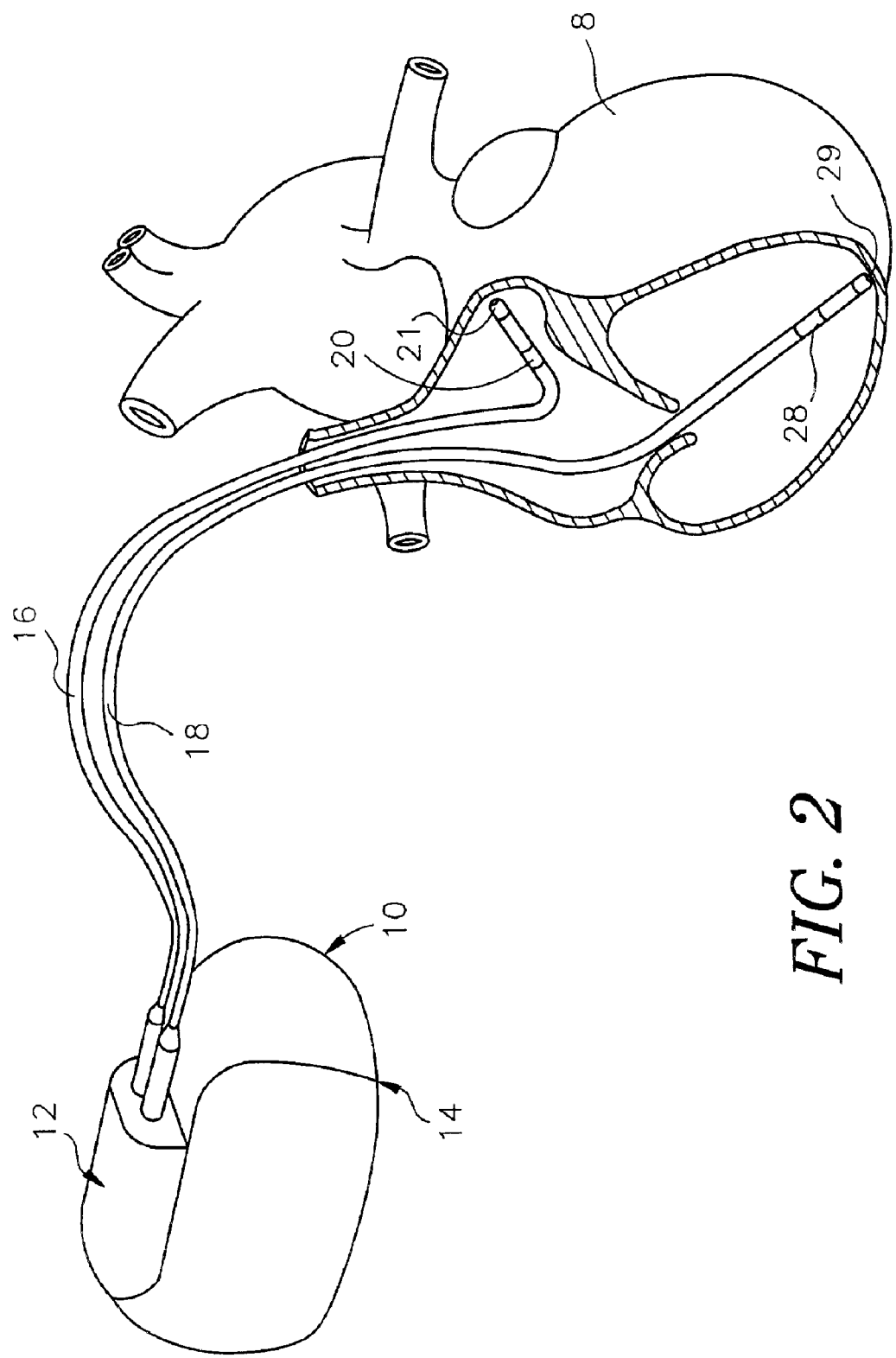
FIG. 2 is an enlarged view of the IMD of FIG. 1 diagrammatically illustrating coupling with the patient's heart in accordance with one embodiment of the invention.

FIG. 2 shows connector module 12 and hermetically sealed enclosure 14 of IMD 10 located near human or mammalian heart 8. Atrial and ventricular pacing leads 16 and 18 extend from connector header module 12 to the right atrium and ventricle, respectively, of heart 8. Atrial electrodes 20 and 21 disposed at the distal end of atrial pacing lead 16 are located in the right atrium. Ventricular electrodes 28 and 29 at the distal end of ventricular pacing lead 18 are located in the right ventricle.

Figure 3:
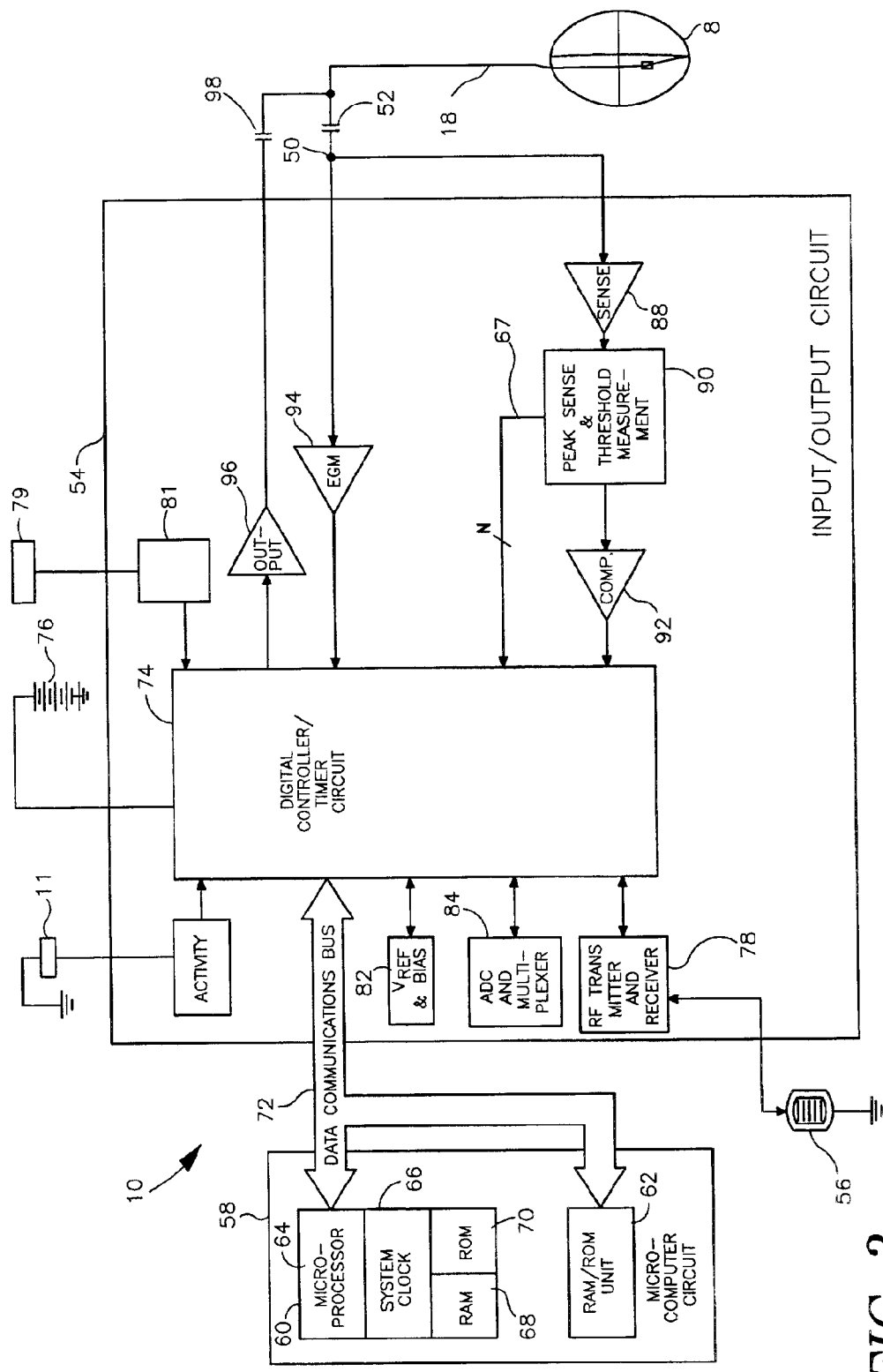
FIG. 3 is a functional block diagram of an IMD in accordance with one embodiment of the present invention where the IMD is a pacemaker.

FIG. 3 is a block diagram illustrating the constituent components of IMD 10 in accordance with one embodiment of the present invention, where IMD 10 is pacemaker having a microprocessor-based architecture. IMD 10 is shown as including activity sensor or accelerometer 11, which is preferably a piezoceramic accelerometer bonded to a hybrid circuit located inside enclosure 14. Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto; similar circuitry and connections not explicitly shown in FIG. 3 apply to lead 16.

In accordance with embodiments of the present invention, blood or hemodynamic sensor 79 may be coupled to input/output circuit 54 via circuitry 81, e.g., buffer circuitry, and/or to digital converters, etc. In some embodiments, hemodynamic sensor 79 is a blood pressure sensor adapted to measure a blood pressure (e.g., systolic pressure) associated with the heart 8 (see FIG. 1). In other embodiments, sensor 79 may be a blood flow sensor adapted to measure the flow rate of blood through one or more portions or chambers of the heart. Various exemplary hemodynamic sensors are described in U.S. Pat. No. 5,799,350 to Ferek-Petric et al. While not illustrated in the Figures, the hemodynamic sensor 79 may be coupled to, or otherwise associated with, one or more leads 16 and 18 (see FIG. 1).

IMD 10 in FIG. 3 is most preferably programmable by means of an external programming unit (not shown in the Figures). One such programmer is the commercially available Medtronic Model 9790 programmer, which is microprocessor-based and provides a series of encoded signals to IMD 10, typically through a programming head which transmits or telemeters radio-frequency (RF) encoded signals to IMD 10. Such a telemetry system is described in U.S. Pat. No. 5,354,319 to Wyborny et al. The programming methodology disclosed in Wyborny et al.'s '319 patent is identified herein for illustrative purposes only. Any of a number of suitable programming and telemetry methodologies known in the art may be employed so long as the desired information is transmitted to and from the pacemaker.

As shown in FIG. 3, lead 18 is coupled to node 50 in IMD 10 through input capacitor 52. Activity sensor or accelerometer 11 is most preferably attached to a hybrid circuit located inside hermetically sealed enclosure 14 of IMD 10. The output signal provided by activity sensor 11 is coupled to input/output circuit 54. Input/output circuit 54 contains analog circuits for interfacing to heart 8, activity sensor 11, antenna 56 and circuits for the application of stimulating pulses to heart 8. The rate of heart 8 is controlled by software-implemented algorithms stored in microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al. On-board circuit 60 preferably includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of IMD 10 is not shown in the Figures. Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,556,063 issued to Thompson et al., or to that disclosed in the above-referenced '319 patent to Wyborny et al. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

$V_{REF}$ and Bias circuit 82 (see FIG. 3) most preferably generates stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled by data bus 72 to digital controller/timer circuit 74, where digital timers and counters establish the overall escape interval of the IMD 10 as well as various refractory, blanking and other timing windows for controlling the operation of peripheral components disposed within input/output circuit 54.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is then provided to comparator/threshold detector 92. By way of example, sense amplifier 88 may correspond to that disclosed in U.S. Pat. No. 4,379,459 to Stein.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al. Output pulse generator 96 provides pacing stimuli to patient's heart 8 through coupling capacitor 98, for example, in response to a pacing trigger signal provided by digital controller/timer circuit 74 each time the escape interval times out, in response to an externally transmitted pacing command or in response to other stored commands as is well known in the pacing art. By way of example, output amplifier 96 may correspond generally to an output amplifier disclosed in U.S. Pat. No. 4,476,868 to Thompson.

The specific embodiments of input amplifier 88, output amplifier 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8.

In some preferred embodiments of the present invention, IMD 10 may operate in various non-rate-responsive modes, including, but not limited to, DDD, DDI, VVI, VOO and VVT modes. In other preferred embodiments of the present invention, IMD 10 may operate in various rate-responsive modes, including, but not limited to, DDDR, DDIR, VVIR, VOOR and VVTR modes. Some embodiments of the present invention are capable of operating in both non-rate-responsive and rate-responsive modes. Moreover, in various embodiments of the present invention, IMD 10 may be programmably configured to operate so that it varies the rate at which it delivers stimulating pulses to heart 8 only in response to one or more selected sensor outputs being generated. Numerous pacemaker features and functions not explicitly mentioned herein may be incorporated into IMD 10 while remaining within the scope of the present invention.

The present invention is not limited in scope to single-sensor or dual-sensor pacemakers, and is not limited to IMD's comprising activity or pressure sensors only. Further, the present invention is not limited in scope to single-chamber pacemakers, single-chamber leads for pacemakers or single-sensor or dual-sensor leads for pacemakers. Thus, various embodiments of the present invention may be practiced in conjunction with more than two leads or with multiple-chamber pacemakers, for example. At least some embodiments of the present invention may be applied equally well in the contexts of single-, dual-, triple- or quadruple- chamber pacemakers or other types of IMD's. See, for example, U.S. Pat. No. 5,800,465 to Thompson et al.

IMD 10 may also be a pacemaker-cardioverter-defibrillator ("PCD") corresponding to any of numerous commercially available implantable PCD's. Various embodiments of the present invention may be practiced in conjunction with PCD's such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless and U.S. Pat. No. 4,821,723 to Baker, Jr. et al.

Figure 4:
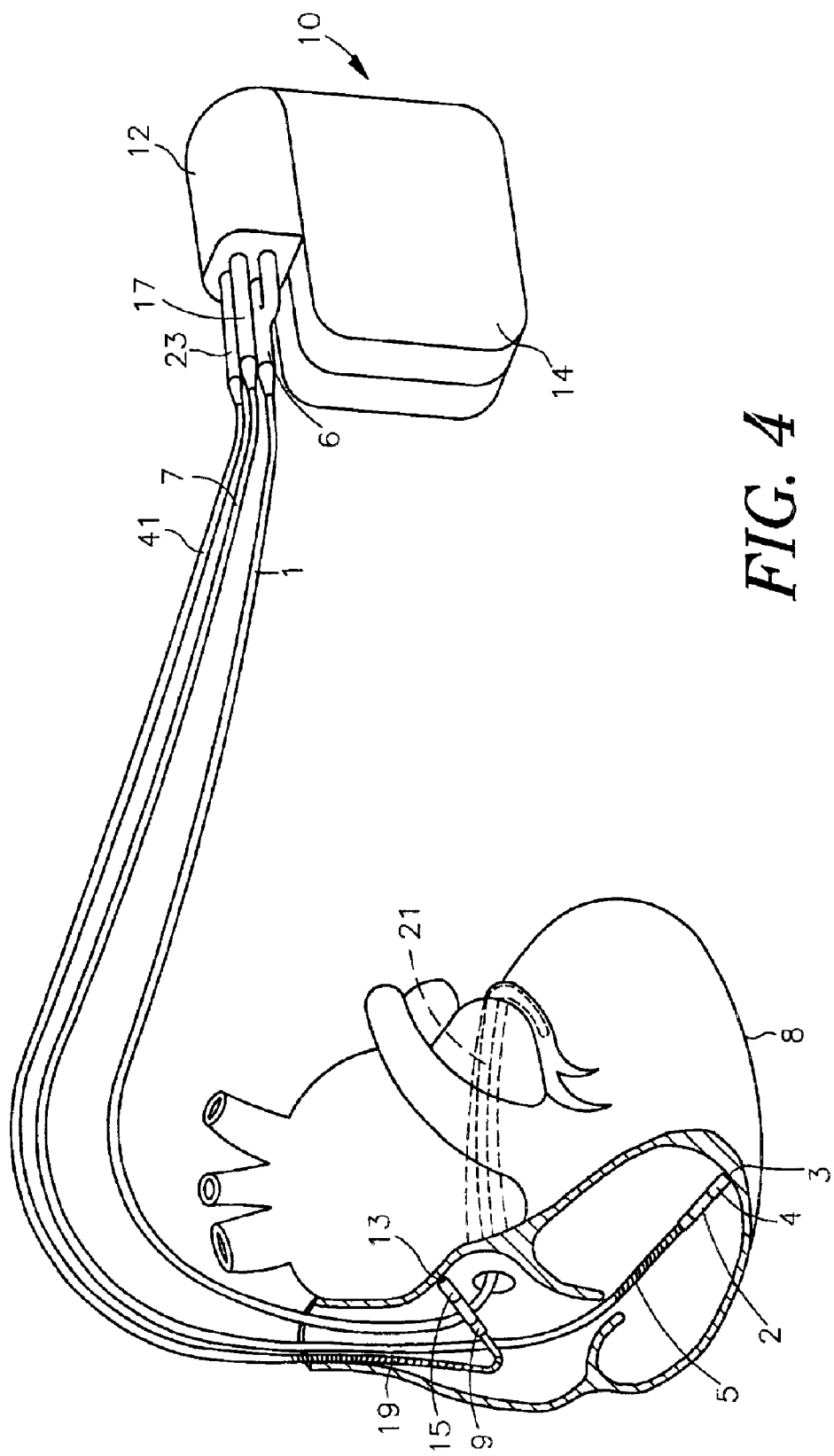
FIG. 4 is an IMD in accordance with another embodiment of the invention, wherein the IMD is an implantable pacemaker-cardioverter-defibrillator (PCD)
Figure 5:
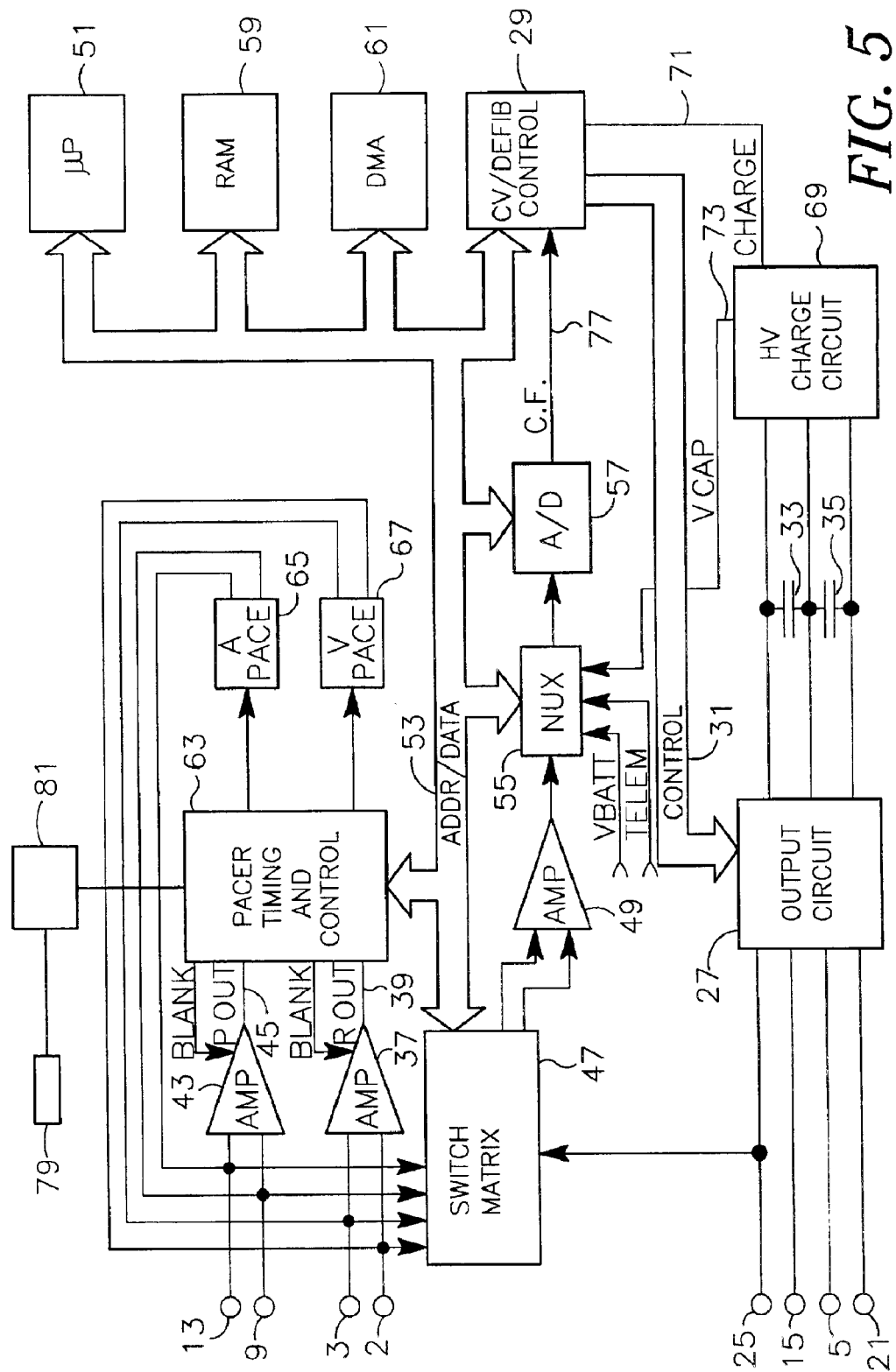
FIG. 5 is a functional block diagram of the PCD of FIG. 4.

FIGS. 4 and 5 illustrate one embodiment of IMD 10 and a corresponding lead set of the present invention, where IMD 10 is a PCD. In FIG. 4, the ventricular lead takes the form of leads disclosed in U.S. Pat. Nos. 5,099,838 and 5,314,430 to Bardy, and includes an elongated insulative lead body 1 carrying three concentric coiled conductors separated from one another by tubular insulative sheaths. Located adjacent the distal end of lead 1 are ring electrode 2, extendable helix electrode 3 mounted retractably within insulative electrode head 4 and elongated coil electrode 5. Each of the electrodes is coupled to one of the coiled conductors within lead body 1. Electrodes 2 and 3 are employed for cardiac pacing and for sensing ventricular depolarizations. At the proximal end of the lead is bifurcated connector 6 which carries three electrical connectors, each coupled to one of the coiled conductors. Defibrillation electrode 5 may be fabricated from platinum, platinum alloy or other materials known to be usable in implantable defibrillation electrodes and may be about 5 cm in length.

The atrial/SVC lead shown in FIG. 4 includes elongated insulative lead body 7 carrying three concentric coiled conductors separated from one another by tubular insulative sheaths corresponding to the structure of the ventricular lead. Located adjacent the J-shaped distal end of the lead are ring electrode 9 and extendable helix electrode 13 mounted retractably within an insulative electrode head 15. Each of the electrodes is coupled to one of the coiled conductors within lead body 7. Electrodes 13 and 9 are employed for atrial pacing and for sensing atrial depolarizations. Elongated coil electrode 19 is provided proximal to electrode 9 and coupled to the third conductor within lead body 7. Electrode 19 preferably is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 17 carrying three electrical connectors, each coupled to one of the coiled conductors.

The coronary sinus lead shown in FIG. 4 assumes the form of a coronary sinus lead disclosed in the above cited '838 patent issued to Bardy, and includes elongated insulative lead body 41 carrying one coiled conductor coupled to an elongated coiled defibrillation electrode 21. Electrode 21, illustrated in broken outline in FIG. 4, is located within the coronary sinus and great vein of the heart. At the proximal end of the lead is connector plug 23 carrying an electrical connector coupled to the coiled conductor. The coronary sinus/great vein electrode 41 may be about 5 cm in length.

The implantable PCD is shown in FIG. 4 in combination with leads 1, 7 and 41, and lead connector assemblies 23, 17 and 6 inserted into connector block 12. Optionally, insulation of the outward facing portion of housing 14 of PCD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other than those shown in FIG. 4 may be practiced in conjunction with the present invention, such as those shown in U.S. Pat. No. 5,690,686 to Min et al.

FIG. 5 is a functional schematic diagram of one embodiment of an implantable PCD of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

The PCD is provided with an electrode system. If the electrode configuration of FIG. 4 is employed, the electrode configuration correspondence may be as follows. Electrode 25 in FIG. 5 includes the uninsulated portion of the housing of the PCD. Electrodes 25, 15, 21 and 5 are coupled to high voltage output circuit 27, which includes high voltage switches controlled by CV/defib control logic 29 via control bus 31. Switches disposed within circuit 27 determine which electrodes are employed and which electrodes are coupled to the positive and negative terminals of the capacitor bank (which includes capacitors 33 and 35) during delivery of defibrillation pulses.

Electrodes 2 and 3 are located on or in the ventricle and are coupled to the R-wave amplifier 37, which preferably takes the form of an automatic gain controlled amplifier providing an adjustable sensing threshold as a function of the measured R-wave amplitude. A signal is generated on R-out line 39 whenever the signal sensed between electrodes 2 and 3 exceeds the present sensing threshold.

Electrodes 9 and 13 are located on or in the atrium and are coupled to the P-wave amplifier 43, which preferably also takes the form of an automatic gain controlled amplifier providing an adjustable sensing threshold as a function of the measured P-wave amplitude. A signal is generated on P-out line 45 whenever the signal sensed between electrodes 9 and 13 exceeds the present sensing threshold. The general operation of R-wave and P-wave amplifiers 37 and 43 may correspond to that disclosed in U.S. Pat. No. 5,117,824, to Keimel et al.

Switch matrix 47 is used to select which of the available electrodes are coupled to wide band (0.5–200 Hz) amplifier 49 for use in digital signal analysis. Selection of electrodes is controlled by the microprocessor 51 via data/address bus 53, which selection may be varied as desired. Signals from the electrodes selected for coupling to bandpass amplifier 49 are provided to multiplexer 55, and thereafter converted to multi-bit digital signals by A/D converter 57, for storage in random access memory 59 under control of direct memory access circuit 61. Microprocessor 51 may employ digital signal analysis techniques to characterize the digitized signals stored in random access memory 59 to recognize and classify the patient's heart rhythm employing any of the numerous signal processing methodologies known in the art.

The remainder of the circuitry is dedicated to the provision of cardiac pacing, cardioversion and defibrillation therapies, and, for purposes of the present invention, may correspond to circuitry known to those skilled in the art. The following exemplary apparatus is disclosed for accomplishing pacing, cardioversion and defibrillation functions. Pacer timing/control circuitry 63 preferably includes programmable digital counters which control the basic time intervals associated with DDD, VVI, DVI, VDD, AAI, DDI and other modes of single and dual chamber pacing well known to the art. Circuitry 63 also preferably controls escape intervals associated with anti-tachyarrhythmia pacing in both the atrium and the ventricle, employing any anti-tachyarrhythmia pacing therapies known in the art.

Intervals defined by pacing circuitry 63 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 51, in response to stored data in memory 59 and are communicated to pacing circuitry 63 via address/data bus 53. Pacer circuitry 63 also determines the amplitude of the cardiac pacing pulses under control of microprocessor 51.

During pacing, escape interval counters within pacer timing/control circuitry 63 are reset upon sensing of R-waves and P-waves as indicated by a signals on lines 39 and 45, and in accordance with the selected mode of pacing on time-out trigger generation of pacing pulses by pacer output circuitry 65 and 67, which are coupled to electrodes 9, 13, 2 and 3. Escape interval counters are also reset on generation of pacing pulses and thereby control the basic timing of cardiac pacing functions, including anti-tachyarrhythmia pacing. The durations of the intervals defined by escape interval timers are determined by microprocessor 51 via data/address bus 53. The value of the count present in the escape interval counters when reset by sensed R-waves and P-waves may be used to measure the durations of R—R intervals, P—P intervals, P-R intervals and R-P intervals, which measurements are stored in memory 59 and used to detect the presence of tachyarrhythmias.

Microprocessor 51 most preferably operates as an interrupt driven device, and is responsive to interrupts from pacer timing/control circuitry 63 corresponding to the occurrence of sensed P-waves and R-waves and corresponding to the generation of cardiac pacing pulses. Those interrupts are provided via data/address bus 53. Any necessary mathematical calculations to be performed by microprocessor 51 and any updating of the values or intervals controlled by pacer timing/control circuitry 63 take place following such interrupts.

Detection of atrial or ventricular tachyarrhythmias, as employed in the present invention, may correspond to tachyarrhythmia detection algorithms known in the art. For example, the presence of an atrial or ventricular tachyarrhythmia may be confirmed by detecting a sustained series of short R—R or P—P intervals of an average rate indicative of tachyarrhythmia or an unbroken series of short R—R or P—P intervals. The suddenness of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann et al., U.S. Pat. No. 4,880,005 issued to Pless et al. and U.S. Pat. No. 4,830,006 issued to Haluska et al. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, IEEE Computer Society Press, pages 167–170. Atrial fibrillation detection methodologies are disclosed in Published PCT Application Ser. No. US92/02829, Publication No. WO92/18198, by Adams et al., and in the article "Automatic Tachycardia Recognition", by Arzbaecher et al., published in PACE, May-June, 1984, pp. 541–547.

As described above with reference to FIG. 3, hemodynamic sensor 79, e.g., pressure or flow sensor, may be electrically coupled to pacer timing and control circuitry 63 via buffer circuitry 81. While shown diagrammatically as a stand-alone component, sensor 79 may be coupled to, or otherwise associated with, one or more of electrodes 9, 13, 2, and 3. Hemodynamic sensor 79 may include any suitable type of hemodynamic sensor, e.g., an intra-cardial blood pressure sensor and/or a flow sensor. The detection of hemodynamically stable versus unstable tachyarrhythmias, as well as other types of tachyarrhythmias, may be supplemented by measuring the blood pressure and/or blood flow using sensor 79.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 51 into the pacer timing and control circuitry 63, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al., U.S. Pat. No. 4,880,005, issued to Pless et al., U.S. Pat. No. 4,726,380, issued to Vollmann et al. and U.S. Pat. No. 4,587,970, issued to Holley et al., may also be employed.

In the event that generation of a cardioversion or defibrillation pulse is required, microprocessor 51 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 51 activates cardioversion defibrillation control circuitry 29, which initiates charging of the high voltage capacitors 33 and 35 via charging circuit 69, under the control of high voltage charging control line 71. The voltage on the high voltage capacitors is monitored via VCAP line 73, which is passed through multiplexer 55 and, in response to reaching a predetermined value set by microprocessor 51, results in generation of a logic signal on Cap Full (CF) line 77 to terminate charging. Thereafter, timing of the delivery of the defibrillation or cardioversion pulse is controlled by pacer timing/control circuitry 63. Following delivery of the fibrillation or tachycardia therapy microprocessor 51 returns the device to q cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al. and U.S. Pat. No. 4,316,472 to Mirowski et al. However, any known cardioversion or defibrillation pulse control circuitry is believed to be usable in conjunction with various embodiments of the present invention. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., may also be employed.

Continuing to refer to FIG. 5, delivery of cardioversion or defibrillation pulses is accomplished by output circuit 27 under the control of control circuitry 29 via control bus 31. Output circuit 27 determines whether a monophasic or biphasic pulse is delivered, the polarity of the electrodes and which electrodes are involved in delivery of the pulse. Output circuit 27 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. Examples of output circuitry for delivery of biphasic pulse regimens to multiple electrode systems may be found in U.S. Pat. No. 4,953,551 to Mehra et al. and in U.S. Pat. No. 4,727,877 to Kallock.

An example of circuitry which may be used to control delivery of monophasic pulses is disclosed in U.S. Pat. No. 5,163,427 to Keimel. Output control circuitry similar to that disclosed in the above cited patent issued to Mehra et al. or U.S. Pat. No. 4,800,883 to Winstrom, may also be used in conjunction with various embodiments of the present invention to deliver biphasic pulses.

Alternatively, IMD 10 may be an implantable nerve stimulator or muscle stimulator such as that disclosed in U.S. Pat. No. 5,199,428 to Obel et al., U.S. Pat. No. 5,207,218 to Carpentier et al. or U.S. Pat. No. 5,330,507 to Schwartz, or an implantable monitoring device such as that disclosed in U.S. Pat. No. 5,331,966 issued to Bennett et al. The present invention is believed to find wide application to any form of implantable electrical device.

Various embodiments of IMD 10 are described above. Attention is now directed to methods for adjusting detection criteria for cardiac pacing and IMDs, e.g., PCDs, that use such methods for detecting specific cardiac arrhythmias, e.g., ventricular tachycardia (VT), ventricular fibrillation (VT).

Various IMDs, such as those described herein, detect arrhythmias such that appropriate therapy may be delivered in response thereto. Such detection as previously described herein may be performed in, for example, pacemakers, PCDs, etc. The following description, for simplicity, shall focus on detection in PCDs. However, such detection techniques, as well as therapy delivered thereafter, is equally applicable to other IMDs as well.

For example, PCDs of the present invention identify the onset of an arrhythmia (e.g., ventricular fibrillation, fast ventricular tachycardia or lower rate ventricular tachycardia) when a cardiac parameter, e.g., heart rate, reaches a zone threshold and remains in the zone for a predetermined number of consecutive counts or "intervals." Counts are based on the occurrence of measured intervals, e.g., R—R intervals, falling within associated heart rate ranges (e.g., R—R interval ranges). For example, should the heart rate rise into the predetermined ventricular tachycardia (VT) zone, the PCD may be programmed to defer detection of VT and delivery of therapy until the sensed heart rate has remained within the VT zone for a predetermined count threshold, e.g., until the number of intervals detected reaches a predetermined threshold value (hereinafter "NID threshold") such as 128. Should the tachycardia correct prior to the count reaching the predetermined NID threshold value, VT is not detected and therapy is not delivered. This technique preserves battery life and patient comfort by avoiding therapy delivery when tachycardia is unsustained.

Generally, each type of arrhythmia (which generally has an associated different therapy) has an associated heart rate zone in which R—R intervals falling within the zone, e.g., below a threshold R—R interval, are counted for use in the detection of the particular type of arrhythmia. For example, an R—R interval counted for VT may typically be about 400 milliseconds (ms), whereas an R—R interval for VF may typically be about 200 ms.

Further, each rate zone may have its own predefined NID threshold required before therapy delivery. For example, "VFNID threshold" for ventricular fibrillation detection may be different than "VTNID threshold" for ventricular tachycardia detection. A discussion of arrhythmia detection via NID may also be found in U.S. Pat. No. 5,312,441 issued to Mader et al.

PCDs of the present invention, however, are able to further distinguish tachycardias based not only on heart rate but also on a hemodynamic parameter. For example, such a hemodynamic parameter may include intracardial blood pressure or blood flow as provided, for example, by using hemodynamic sensor 79 discussed above with respect to FIGS. 3 and 5.

Figure 6:
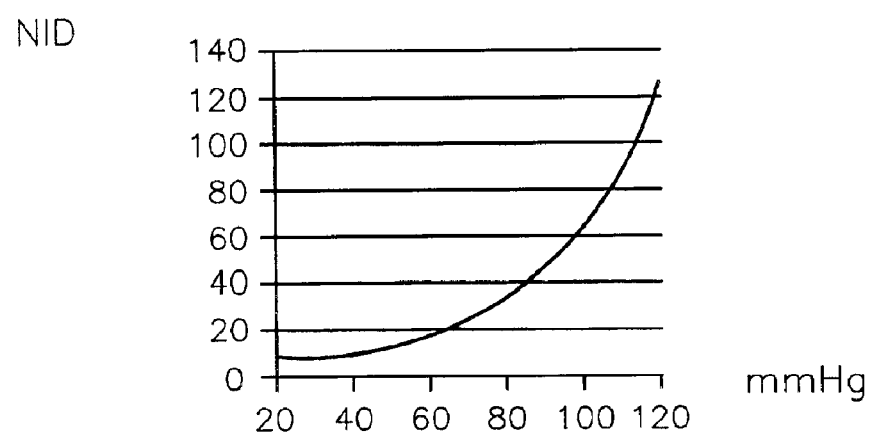
FIG. 6 is a graph illustrating an exemplary relationship between blood pressure and number of intervals detected (NID) threshold.

In general, PCDs of the present invention utilize hemodynamic sensor 79 to adjust the predefined NID threshold so that therapy may be delivered more quickly when hemodynamic instability is detected. FIG. 6 illustrates an exemplary relationship between NID threshold and a hemodynamic characteristic such as blood pressure (measured in millimeters-mercury (mm-Hg)) as detected by sensor 79. As the graph illustrates, when blood pressure is stable, e.g., 120 mm-Hg, NID threshold is set higher, e.g., 128. When blood pressure falls to 100 mm-Hg, NID threshold is reset to, for example, 60. Should blood pressure be detected at or below 40 mm-Hg, the NID threshold may be reset even lower, e.g., 8. Of course, the graph of FIG. 6 is exemplary only and the relationship between blood pressure and NID threshold may be customized for different scenarios as well as for individual patients. For instance, the relationship could be characterized by discrete steps rather than the varying slopes or curves as shown.

Accordingly, embodiments of the present invention permit adjustable NID thresholds based on input from hemodynamic sensor 79. As a result, PCDs are able to deliver therapy more rapidly in the event hemodynamically unstable tachycardia occurs, e.g., NID threshold may be lowered. As used herein, the term "hemodynamically unstable" refers to a substantial drop in blood pressure which may be either initiated by or triggered in response to increased heart rate. By delivering therapy more quickly, the syncope often accompanying hemodynamically unstable tachycardias may be avoided. While providing more rapid therapy delivery in the event of a hemodynamically unstable tachycardia, methods of the present invention may defer therapy delivery, e.g., leave the NID threshold unchanged from its preprogrammed value, when blood pressure remains normal, thus preventing premature therapy delivery in the event of an unsustained hemodynamically stable tachycardia.

Figure 7:
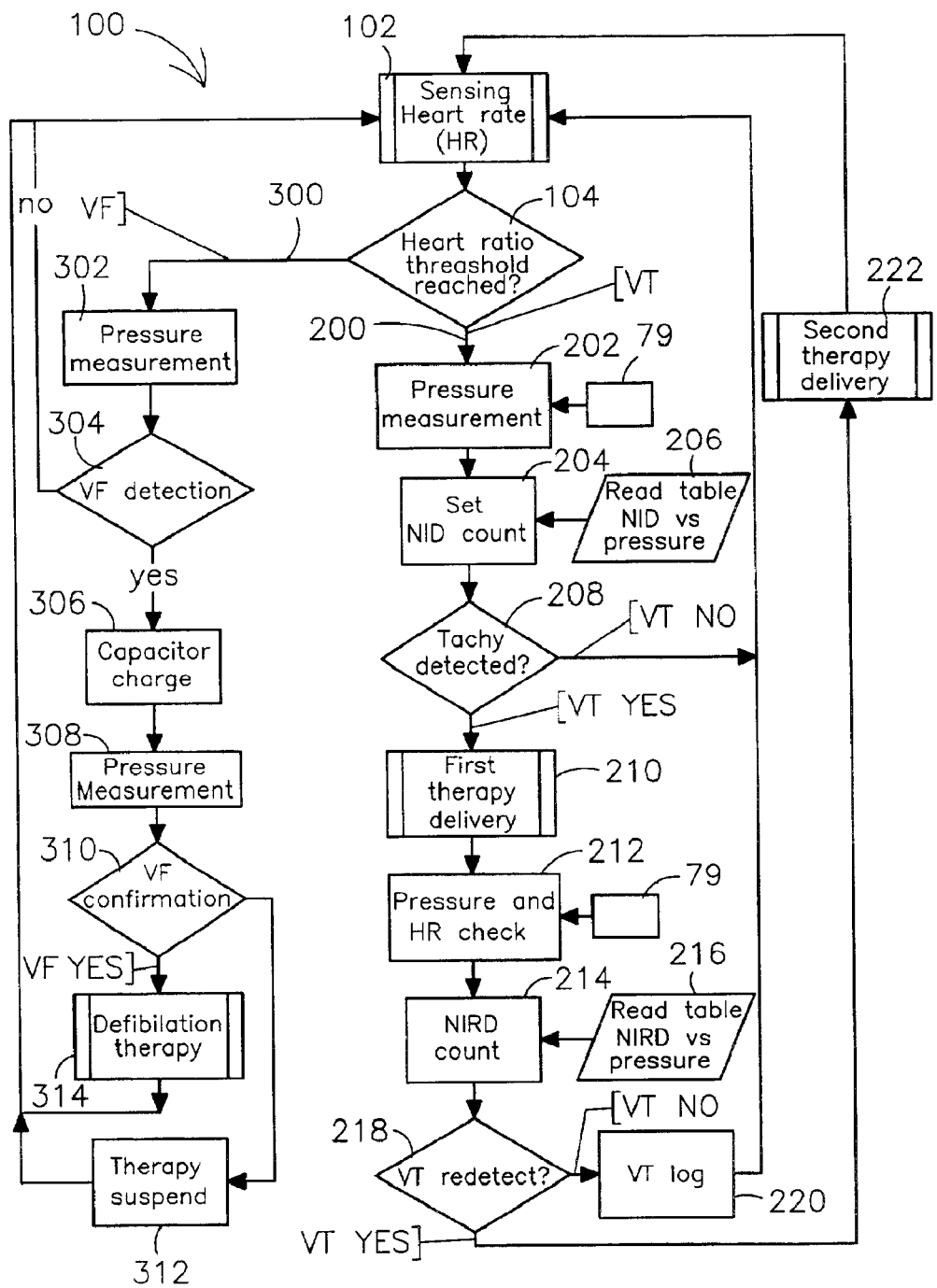
FIG. 7 is a flow chart illustrating a detection subroutine in accordance with one embodiment of the invention.

FIG. 7 is a flow chart illustrating an exemplary subroutine 100 for use with a PCD in tachycardia detection in accordance with one embodiment of the invention. For purposes of explanation, subroutine 100 is represented as having only two therapies activated for particular types of arrhythmia, VF and VT. However, those of skill in the art will realize that most any therapy for the same or different types of arrhythmia may be included without departing from the scope of the invention.

At 102, the PCD microprocessor (e.g., microprocessor 51 of FIG. 5) continuously senses heart rate (e.g., R—R interval) using signals from one or more sensing leads such as leads 2 and 3 of FIG. 5. The sensed heart rate (e.g., R—R interval) is compared to one or more heart rate threshold values (e.g., R—R interval threshold values) at 104. If the heart rate is greater than the heart rate threshold value (e.g., if the R—R interval is less than the R—R interval threshold value) for VT (e.g., greater than 160 beats per minute (bpm)), then a VT detection subroutine 200 is initiated. If the sensed heart rate exceeds the heart rate threshold value for VF (e.g., greater than 200 bpm), than a VF detection subroutine 300 as further described below is initiated.

Once the heart rate threshold value for VT is satisfied, blood pressure is measured and recorded, preferably continuously throughout the VT episode, at 202 using blood pressure sensor 79. Based on the blood pressure measurement, a NID threshold is set in accordance with a predefined relationship of NID threshold to blood pressure. For example, the NID threshold may be calculated, e.g., read from a look-up table, at 206 and set at 204. The NID threshold may be programmed based upon a NID threshold—blood pressure function such as that exemplified in FIG. 6 and stored in PCD memory (e.g., RAM or ROM memory).

With the NID threshold adjusted, consecutive counts of R—R intervals that are shorter than the R—R interval threshold value (e.g., heart rate greater than the heart rate threshold) for VT are monitored and compared to the NID threshold at 208. If the number of intervals counted does not satisfy the NID threshold, e.g., the number of intervals counted does not meet or exceed the NID threshold, then tachycardia is not detected and the subroutine returns to heart rate (e.g., R—R interval) sensing at 102.

If, on the other hand, the number of intervals satisfies the NID threshold, then a first therapy is delivered at 210. The first therapy may include any suitable therapy for treating tachycardia, e.g., anti-tachycardia pacing such as extra stimuli or bursts of stimuli.

Following delivery of the first therapy, the heart rate (e.g., R—R intervals) is again compared to preprogrammed thresholds, e.g., VT, at 212 to detect whether tachycardia still persists after first therapy delivery at 210. Further, blood pressure is measured. Although not illustrated, if the heart rate has slowed to normal levels, the subroutine may return to heart rate (e.g., R—R interval) sensing at 102.

In other embodiments, a number of intervals redetected (NIRD) threshold is set at 214 in accordance with a predefined relationship of NIRD threshold to blood pressure determined at 216, e.g., read from a lookup table, similar to 204 and 206 described above. The NIRD threshold may be based upon the same relationship used at 206 or on a modification thereof.

Again, the number of consecutive R—R intervals that are shorter than the R—R threshold value for VT are counted and compared with the set NIRD threshold at 218. If the number of counted intervals fails to reach the NIRD threshold, e.g., the tachycardia is unsustained, then tachycardia is not redetected. The VT episode may then be logged in memory at 220 before the subroutine returns to heart rate (e.g., R—R interval) sensing at 102.

If the number of counted intervals satisfies the NIRD threshold at 218, then a second therapy is delivered at 222. The second therapy may include any one of a number of therapies suitable for treating tachycardias that are unresponsive to pacing, e.g., defibrillation shock therapy. Once the second therapy is delivered at 222, the subroutine returns to heart rate (e.g., R—R interval) sensing at 102.

Preferably, blood pressure and heart rate are sensed continuously and the detection parameters set accordingly. As a result, a worsening tachycardia is quickly detected and therapy delivery is accelerated based upon the principles described and illustrated herein.

Variations of the subroutine illustrated in FIG. 7 may be made without departing from the scope of the present invention. For example, logging, such as that illustrated at 220, may be incorporated at any point in the process and may record most any sensed parameter, e.g., heart rate, blood pressure, etc.

As mentioned, subroutine 100, as illustrated, may also have VF detection and therapy activated. If the sensed heart rate (e.g., R—R interval) at 104 is greater than a heart rate threshold value (e.g., R—R interval threshold value) for VF (e.g., greater than 200 bpm), then the VF subroutine 300 is initiated.

Once the heart rate threshold value for VF is satisfied, blood pressure is measured and recorded at 302 using blood pressure sensor 79. VF (as opposed to a false positive associated with other physiological factors, e.g., EMI, muscle contractions, which may be, for example, determined by activity sensor 11 of FIG. 3) is detected at 304 with the use of the blood pressure measurement at 302. If VF is not detected, then the subroutine returns to heart rate sensing at 102. If VF is detected, then a capacitor is charged at 306 for delivery of therapy. A pressure measurement is again measured at 308 to confirm VF is sustained before therapy delivery. If VF is unsustained, e.g., blood pressure at 308 is normal, then therapy is suspended at 312 and the subroutine returns to heart rate sensing at 102.

If VF is confirmed at 310, the PCD will initiate defibrillation therapy delivery at 312. Once therapy is delivered, the subroutine returns to heart rate sensing at 102. As with VT identification, cardiac parameters may be logged and stored for later interrogation by medical personnel.

The subroutine illustrated in FIG. 7 thus provides adjustable detection criteria for VT based upon a hemodynamic parameter such as intracardial blood pressure. Apparatus and methods of the present invention preferably distinguish hemodynamically stable from hemodynamically unstable tachycardias by varying the threshold number of intervals detected before therapy delivery based on blood pressure. Blood pressure measurements may be used not only to vary the NID threshold, but also to distinguish other sustained from unsustained arrhythmias, e.g., VF. It will be recognized that other hemodynamic parameters, such as blood flow, may also be used to adjust the NID threshold.

Figure 8:
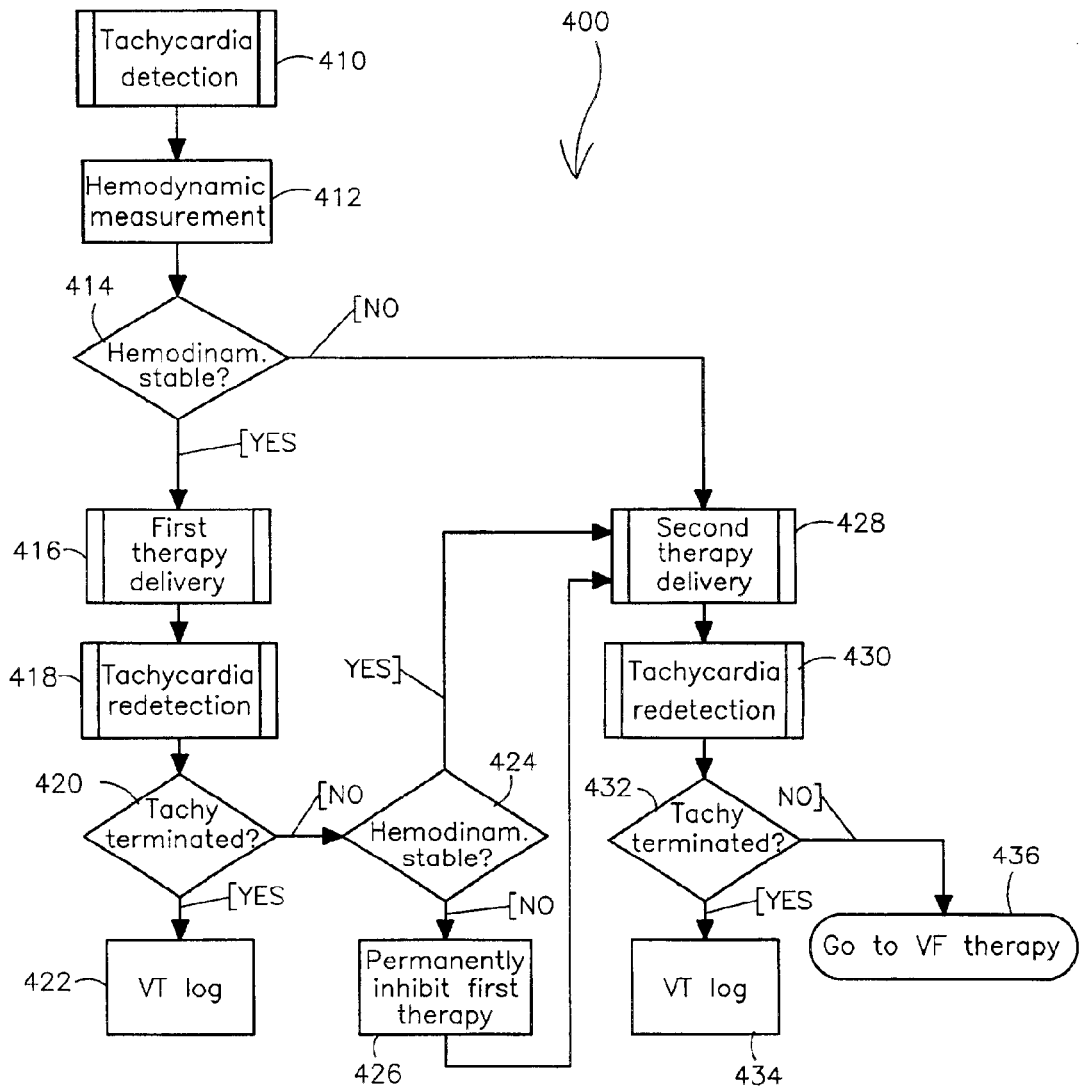
FIG. 8 is a flow chart illustrating a detection subroutine in accordance with another embodiment of the invention.

In addition to using hemodynamic sensor 79 for adjusting NID and determining sustained from unsustained arrhythmia as described with reference to FIG. 7, sensor 79 may be used in conjunction with a tiered therapy technique 400 as illustrated in FIG. 8. Tiered therapy is beneficial as it permits less aggressive therapy for hemodynamically stable tachycardia and, correspondingly, more aggressive therapy in the event of an hemodynamically unstable tachycardia.

Another benefit of the tiered therapy techniques described and illustrated herein is that therapies that provoke hemodynamic instability may be permanently inhibited. For example, a therapy delivered in response to a stable tachycardia may itself provoke hemodynamic instability. Accordingly, in addition to discriminating between successful and unsuccessful therapies, PCDs incorporating the tiered therapy techniques described herein are also able to discriminate, and preferably disable, therapies that destabilize hemodynamics.

FIG. 8 illustrates an exemplary tiered therapy method 400. Tachycardia detection may be provided using any suitable method known in the art. More preferably, tachycardia detection may be performed using a blood pressure—adjustable NID threshold technique as described above.

When tachycardia is detected, a hemodynamic parameter, e.g., blood pressure and/or flow, is measured and recorded at 412 as previously described herein (see FIG. 7). Preferably, blood pressure is continuously monitored and recorded.

If the tachycardia is determined to be hemodynamically stable at 414, e.g., blood pressure is within normal ranges, then a first therapy is delivered at 416. Appropriate therapies for hemodynamically stable tachycardia may include those therapies known in the art, e.g., anti-tachycardia pacing, such as extra stimuli or bursts of stimuli, ramp pacing, and ramp plus pacing. Detection of hemodynamically unstable tachycardia at 414 leads to delivery of a more aggressive second therapy at 428. The second therapy may include such therapies as synchronous shock-cardioversion, antiarrhythmic drug delivery, and stimulation of the autonomic nervous system.

Tachycardia redetection may then be employed at 418 to verify whether tachycardia was successfully treated with the first therapy. Once again, the method of detection may be based upon an adjustable NID threshold as described previously herein or any other detection method. If tachycardia has terminated at 420, then the event is logged and recorded in the VT log at 422 and stored in the PCD's memory for later interrogation.

If the first tachycardia therapy is determined to be unsuccessful at 420 and tachyarrhythmia continues, a second hemodynamic measurement is checked at 424 using similar methods as described above regarding the hemodynamic measurement at 412, e.g., a continuously monitored blood pressure. If the tachycardia is determined to be stable, then the second therapy is delivered at 428. However, where hemodynamic instability is detected at 424, the first therapy, e.g., anti-tachycardia pacing, is permanently disabled at 426. That is, the first therapy is disabled as it was not only unsuccessful but also because it most likely introduced hemodynamic instability.

After disabling the first therapy at 426, the subroutine passes to delivery of the second therapy at 428.

Following delivery of the second therapy at 428, tachycardia redetection occurs at 430 to determine whether the second therapy successfully terminated the tachycardia. If tachycardia has been terminated at 432, then the event is recorded in the VT log at 434 and stored in the PCD's memory for later interrogation. If tachycardia has not been terminated at 432, then the algorithm proceeds to VF therapy at 436. Suitable VF therapies may include high-voltage shock-defibrillation and antiarrhythmic drug delivery.

Figure 9:
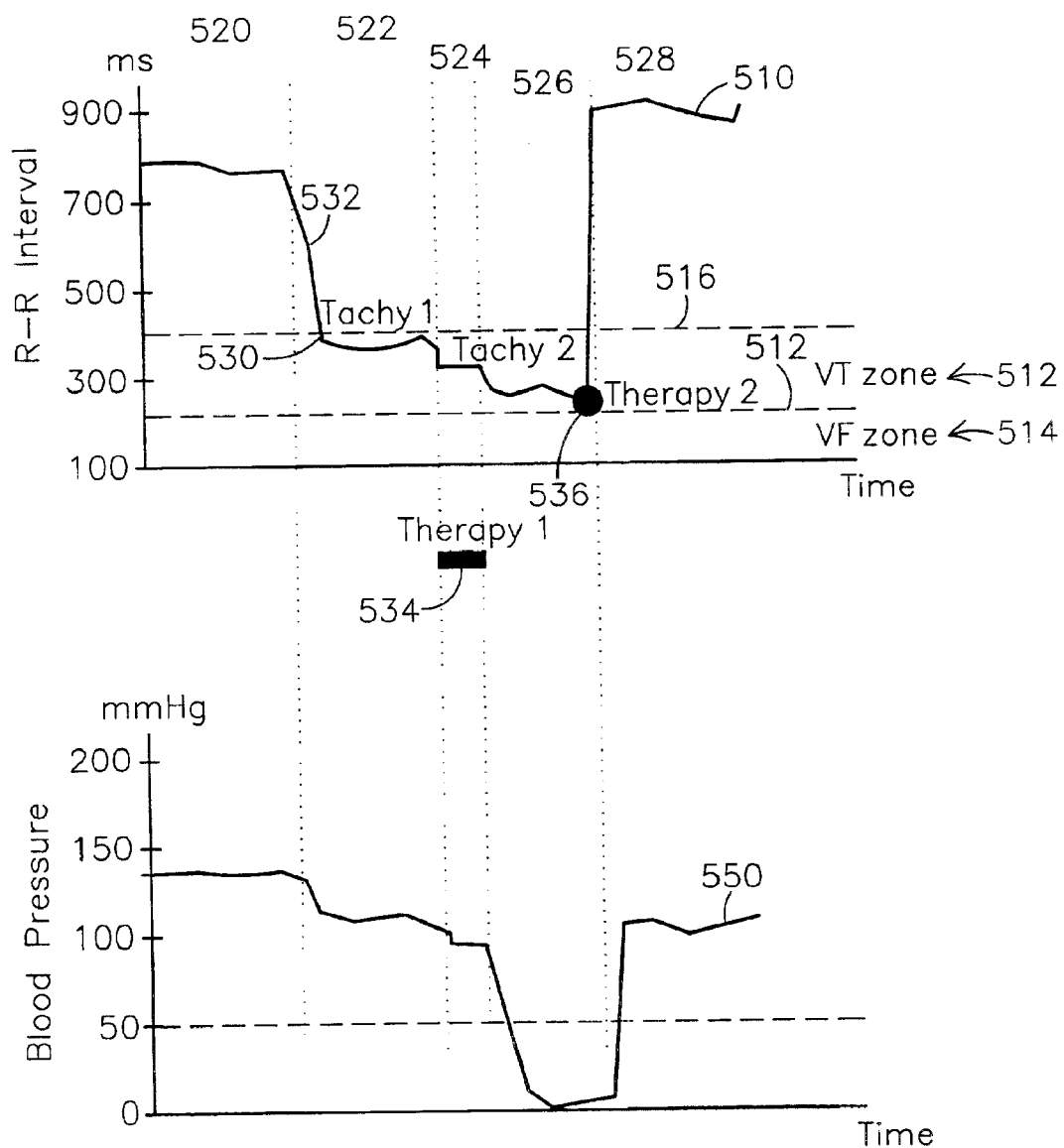
FIG. 9 is a graph showing recorded cardiac cycles, including the relationship between R—R interval (i.e., heart rate) and blood pressure relative to time, respectively.

FIG. 9 illustrates a graph 510 of arrhythmia detection and treatment as may be obtained by interrogation of a PCD's memory log. This figure further corresponds to and illustrates the tiered therapy delivery described above and illustrated in FIG. 8. The upper curve 510 includes the heart rate, e.g., the R—R interval (in milliseconds), as a function of time. The lower curve 550 illustrates the systemic blood pressure expressed in mm-Hg, also with respect to time.

A VT zone 512 is defined by a VT threshold 516 while a VF zone 514 is defined by a VF threshold 518. Any R—R interval detected that is less than VT threshold 516 will activate a tachycardia detection subroutine while any R—R interval detected below VF threshold 518 will initiate a fibrillation detection subroutine. In this particular embodiment, VT threshold 516 is equal to 400 ms while VF threshold is equal to 225 ms. However, these values may vary depending on the particular PCD and patient.

During tachycardia in this illustrative situation, the R—R interval declines below VT threshold 516 as indicated by point 530 in first tachycardia region 522 (corresponding to detection at 410 in FIG. 8). After determining that blood pressure (curve 550) is within an acceptable range (see block 414 in FIG. 8), a first therapy may be delivered at 534 in first therapy delivery region 524.

Region 520 indicates normal heart function, e.g., normal R—R interval rhythm (heart rate) and blood pressure. Tachycardia manifests as a sudden R—R heart rate increase, e.g., a sudden R—R interval drop, indicated by segment 532. When the interval falls below VT threshold 516 into VT zone 512, tachycardia is detected. In the illustrated embodiment of FIG. 9, blood pressure remains stable during the first tachycardia. As a result, the first therapy is delivered at 534 in the first therapy region 524 (block 416 in FIG. 8). Tachycardia redetection is then performed at second tachycardia region 526 (block 418 in FIG. 8) and indicates an R—R interval still below VT threshold 516. Further, blood pressure in second tachycardia region 526 (block 424 in FIG. 8) indicates hemodynamic instability. As a result, first therapy 534 is disabled (block 426 in FIG. 8) and a second therapy at 536 is delivered at 536 (block 428 in FIG. 8). In this example, second therapy 536 was successful, as indicated by the R—R interval above the VT threshold 516 and normal blood pressure (as seen in curve 550) in post therapy region 528.

The complete disclosure of the patents, patent documents, and publications cited in the Background, Detailed Description of the Embodiments and elsewhere herein are incorporated by reference in their entirety as if each were individually incorporated.

The preceding specific embodiments are illustrative of the practice of the invention. It is to be understood, therefore, that other expedients known to those skilled in the art or disclosed herein may be employed without departing from the invention or the scope of the appended claims. For example, the present invention is not limited to the use of adjustable NID thresholds in PCDs, but such concepts may, as mentioned above, be used with any other passive apparatus, implanted or external. The present invention further includes within its scope methods of making and using the programmers and systems described herein above.

What is claimed is:

1. A method for distinguishing a hemodynamically stable tachycardia from a hemodynamically unstable tachycardia, comprising:
   sensing a heart rate;
   comparing the heart rate to a heart rate threshold value;
   monitoring a blood pressure sensor upon detecting the heart rate greater than the heart rate threshold value to detect a substantial drop in blood pressure;
   invoking a first number of intervals detected (NID) threshold up detecting the heart rate greater than the heart rate threshold value if a substantial drop in blood pressure is not detected;
   invoking a second NID threshold that is lower than the first NID threshold upon detecting a substantial drop in blood pressure;
   counting a consecutive number at intervals in which the heart rate is greater than the heart rate threshold value;
   making a tachycardia detection if the consecutive number of intervals satisfies the invoked NID threshold, the tachycardia detection being a detection of a hemodynamically stable tachycardia if the first NID threshold is invoked and the tachycardia detection being a detection of a hemodynamically unstable tachycardia if the second NID threshold is invoked; and
   delivering a first low power tachycardia response therapy upon making a tachycardia detection that the tachycardia is a hemodynamically stable tachycardia and delivering a second high power tachycardia response therapy upon detection that the tachycardia that is a hemodynamically unstable tachycardia.

2. A pacing apparatus, comprising:
   sensing and pacing circuitry for sensing cardiac activity and generating pacing pulses;
   a blood pressure sensor to detect a substantial drop in blood pressure; and
   controller circuitry coupled to the blood pressure sensor, the controller circuitry operable to:
   sense a heart rate;
   compare the heart rate to a heart rate threshold value;
   monitor a blood pressure sensor upon detecting the heart rate greater than the heart rate threshold value to detect a substantial drop in blood pressure;
   invoke a first number of intervals detected (NID) threshold upon detecting the heart rate greater than the heart rate threshold value if a substantial drop in blood pressure is not detected;
   invoke a second NID threshold that is lower than the first NID threshold upon detecting a substantial drop in blood pressure;
   count a consecutive number of intervals in which the heart rate is greater than the heart rate threshold value;
   make a tachycardia detection if the consecutive number of intervals satisfies the invoked NID threshold, the tachycardia detection being a detection of a hemodynamically stable tachycardia if the first NID threshold is invoked and the tachycardia detection being detection of a hemodynamically unstable tachycardia if the second NID threshold is invoked; and
   deliver a low power tachycardia response therapy upon making a tachycardia detection that the tachycardia is a hemodynamically stable tachycardia and delivering a high power tachycardia response therapy upon detection that the tachycardia that is a hemodynamically unstable tachycardia.

3. A method according to claim 1, wherein the low power tachycardia response therapy comprises one of an antitachycardia pacing regimen and a cardioversion therapy.

4. A method according to claim 1, wherein the high power tachycardia response therapy comprises a defibrillation therapy.

5. A method according to claim 4, wherein the defibrillation therapy comprises at least thirty joules of delivered energy.

6. A method according to claim 4, wherein the defibrillation therapy comprises a ventricular defibrillation therapy.

7. A method according to claim 2, wherein the low power tachycardia response therapy comprises one of an antitachycardia pacing regimen and a cardioversion therapy.

8. A method according to claim 2, wherein the high power tachycardia response therapy comprises a defibrillation therapy.

9. A method according to claim 8, wherein the defibrillation therapy comprises at least thirty joules of delivered energy.

10. A method according to claim 8, wherein the defibrillation therapy comprises a ventricular defibrillation therapy.

11. A computer readable medium for storing executable instructions to operate a medical device and cause said medical device to distinguish a hemodynamically stable tachycardia from a hemodynamically unstable tachycardia, comprising:
   instructions for sensing a heart rate;
   instructions for comparing the heart rate to a heart rate threshold value;
   instructions for monitoring a blood pressure sensor upon detecting the heart rate greater than the heart rate threshold value to detect a substantial drop in blood pressure;
   instructions for invoking a first number of intervals detected (NID) threshold upon detecting the heart rate greater than the heart rate threshold value if a substantial drop in blood pressure is not detected;

instructions for invoking a second NID threshold that is lower than the first NID threshold upon detecting a substantial drop in blood pressure;

instructions for counting a consecutive number of intervals in which the heart rate is greater than the heart rate threshold value;

instructions for making a tachycardia detection if the consecutive number of intervals satisfies the invoked NID threshold the tachycardia detecting being a detection of a hemodynamically stable tachycardia if the first NID threshold is invoked and the tachycardia detection being a detection of a hemodynamically unstable tachycardia if the second NID threshold is invoked; and instructions for delivering a first low power tachycardia response therapy upon making a tachycardia detection that the tachycardia is a hemodynamically stable tachycardia and delivering a second high power tachycardia response therapy upon detection that the tachycardia that is a hemodynamically unstable tachycardia.

12. A medium according to claim 11, wherein the low power tachycardia response therapy comprises one of an anti-tachycardia pacing regimen and a cardioversion therapy.

13. A medium to claim 11, wherein the high power tachycardia response therapy comprises a defibrillation therapy.

14. A medium according to claim 13, wherein the defibrillation therapy comprises at least thirty joules of delivered energy.

15. A medium according to claim 13, wherein the defibrillation therapy comprises a ventricular defibrillation therapy.

* * * * *

UNITED STATES PATENT AND TRADEMARK OFFICE
CERTIFICATE OF CORRECTION

PATENT NO. : 6,873,870 B2
APPLICATION NO. : 09/843914
DATED : March 29, 2005
INVENTOR(S) : Bozidar Ferek-Petric It is certified that error appears in the above-identified patent and that said Letters Patent is hereby corrected as shown below:

Col. 17, line 37, please delete "Threshold up detecting" and insert --threshold upon detecting--.

Col. 17, line 43, please delete "number at intervals" and insert --number of intervals--.

Col. 19, line 9, please delete "threshold the" and insert --threshold, the--.

Signed and Sealed this

Second Day of January, 2007

JON W. DUDAS
*Director of the United States Patent and Trademark Office*